United States Patent
Alferiev et al.

(10) Patent No.: US 11,633,485 B2
(45) Date of Patent: Apr. 25, 2023

(54) CLEAVABLE ESTERS FOR NANOCARRIER-BASED CANCER THERAPY

(71) Applicant: The Children's Hospital of Philadelphia, Philadelphia, PA (US)

(72) Inventors: Ivan Alferiev, Clementon, NJ (US); Michael Chorny, Huntingdon Valley, PA (US); Garrett M. Brodeur, Wynnewood, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 648 days.

(21) Appl. No.: 16/494,101

(22) PCT Filed: Mar. 13, 2018

(86) PCT No.: PCT/US2018/022146
§ 371 (c)(1),
(2) Date: Sep. 13, 2019

(87) PCT Pub. No.: WO2018/169934
PCT Pub. Date: Sep. 20, 2018

(65) Prior Publication Data
US 2020/0061199 A1    Feb. 27, 2020

Related U.S. Application Data

(60) Provisional application No. 62/471,027, filed on Mar. 14, 2017.

(51) Int. Cl.
A61K 31/16 (2006.01)
A61K 47/55 (2017.01)
A61P 35/00 (2006.01)
A61K 31/165 (2006.01)
A61K 31/355 (2006.01)
A61K 31/454 (2006.01)

(52) U.S. Cl.
CPC ............ A61K 47/55 (2017.08); A61K 31/165 (2013.01); A61K 31/355 (2013.01); A61K 31/454 (2013.01); A61P 35/00 (2018.01)

(58) Field of Classification Search
CPC .............................. A61K 31/165; A61K 47/55
See application file for complete search history.

(56) References Cited

U.S. PATENT DOCUMENTS

| | | |
|---|---|---|
| 2008/0045559 A1 | 2/2008 | Zhang |
| 2011/0112131 A1 | 5/2011 | Holtman et al. |
| 2013/0101056 A1 | 4/2013 | Su et al. |
| 2015/0119388 A1 | 4/2015 | Alferiev et al. |

FOREIGN PATENT DOCUMENTS

| | | |
|---|---|---|
| WO | 2006027711 A1 | 3/2006 |
| WO | 2012092339 A2 | 7/2012 |
| WO | 2013188727 A2 | 12/2013 |
| WO | 2016144637 A1 | 9/2016 |

OTHER PUBLICATIONS

Russian Office Action for Russian Application No. 201992157, dated Nov. 26, 2020, with translation, 6 pages.
International Search Report and Written Opinion for International Application No. PCT/US2018/022146, dated May 25, 2018—5 pages.
Extended European Search Report for European Application No. 18 767 318.1, dated Oct. 16, 2020, 11 pages.
Anonymous: "SN-22—Wikipedia", Jun. 23, 2020, pp. 1-2, XP055733547, Retrieved from the Internet: https://en.wikipedia.org/wiki/SN-22 [retrieved on Sep. 24, 2020].
Anonymous: "78287-27-1 / 7-Ethyl Camptothecin / (4S)-4,11-Diethyl-4-hydroxy-1H-pyrano[3',4':6,7]indolizino[1,2-b]quinoline-3,14(4H,12H,)-dione; 7-Ethyl-20(S)-camptothecin; SN22", Catalogue No. E900830, Jan. 1, 2020, pp. 1-5, XP055733558, Retrieved from the Internet: https://www.trc-canada.com/product-detail/?CatNum=E900830 [retrieved on Sep. 24, 2020].
International Preliminary Report on Patentability and Written Opinion for International Application No. PCT/US2018/022146, dated Sep. 17, 2019, 5 pages.
European Communication pursuant to Article 94(3) for European Application No. 18 767 318.1, dated Sep. 23, 2022, 4 pages.

*Primary Examiner* — Shawquia Jackson
(74) *Attorney, Agent, or Firm* — RatnerPrestia

(57) ABSTRACT

A co-drug according to Formula (I) or Formula (II) is provided,

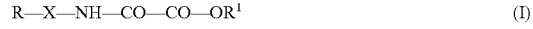

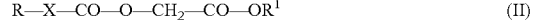

wherein R is a tocol moiety, a tocol analog moiety, or a capsaicinoid moiety; X is a direct bond or a linking group; and $OR^1$ is the residue of an anticancer or antirestenotic agent bearing at least one hydroxyl group by which the $CO-OR^1$ ester linkage is formed. Nanoparticles that include the abovementioned co-drug are also provided, as well as a method of treating a cancer patient that includes administering an effective amount of the co-drug or nanoparticles.

12 Claims, 3 Drawing Sheets

CLEAVABLE ESTERS FOR NANOCARRIER-BASED CANCER THERAPY

CONTINUING APPLICATION INFORMATION

This is the national phase of International Application No. PCT/US18/22146, filed 2018 Mar. 13, which claims priority to U.S. Provisional Application No. 62/471,027, filed 2017 Mar. 14. The disclosure of each of these applications is incorporated herein by reference in its entirety for all purposes.

BACKGROUND

Neuroblastoma (NB) remains the most common and deadly solid tumor of childhood accounting for 8-10% of all childhood cancers, and 15% of deaths from cancer in children. Despite improvements in the cure rate for other pediatric neoplasms, the survival rate for patients with NB has lagged behind.

The intensive, multimodality therapy currently used in the clinic fails in over half of the patients (50-60% of patients experience a relapse with no curative salvage treatment options), with the most formidable therapeutic challenge presented by the non-responder patient subgroup, defined as an "ultrahigh" risk category.

High-risk NB with its highly diverse etiology and prevalence of biologically unfavorable variants is currently approached by potent anticancer agents as a first-line treatment, including topoisomerase I inhibitors of the camptothecin family: topotecan and irinotecan. However, their clinical use in the context of aggressive disease remains suboptimal, yielding poor results in relapsed or refractory NB patients due to dose-limiting side effects and acquired drug resistance.

Importantly, treatment failure in these patients was shown to be associated with an increase in threshold drug levels required for effectively suppressing NB cell growth by 1-3 orders of magnitude, reaching values not achievable clinically. Thus, to combat refractory NB, and other forms of cancer, there is a need for alternative therapeutic approaches, which can markedly enhance intratumoral delivery and extend drug presence at therapeutically effective drug levels without increasing systemic exposure.

Redox-silent mitocans include a variety of structures capable of exhibiting anticancer activity and cooperating with different types of chemotherapeutics in vitro and in vivo. The majority of redox-silent mitocans are carboxylic acids incorporating the highly hydrophobic tocopherol in which the phenolic hydroxyl group is blocked, rendering the compounds redox-silent. When employed as part of a co-drug conjugate, they can readily increase hydrophobicity to Log $P_{o/w}$ values >9 and promote compatibility with the matrix of nanoparticles used to deliver them. The hydrophobizing effect is essential for preventing rapid and complete dissociation from the carrier, while the acidic carboxylate function is thought to be a prerequisite for the pharmacologic activity.

For example, tocopheryloxyacetic acid has been reported as a mitocan that is stable against unblocking of the phenolic hydroxyl group, thus maintaining redox-silence.

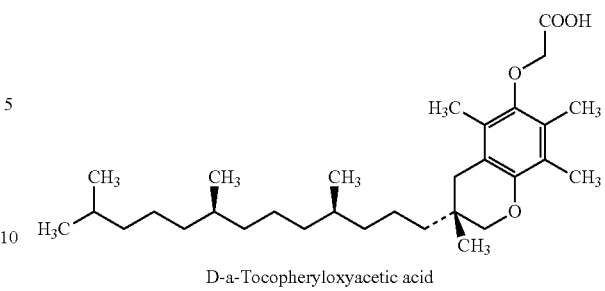

D-a-Tocopheryloxyacetic acid

Although tocopheryloxyacetic acid and other tocopherol derivatives show promise as anticancer and antiproliferative agents, enhancing the effects of redox-silent mitocans with pharmacologically complementary compounds and enabling their effective delivery in active form remains a challenge, and improvements in this respect would be welcome.

SUMMARY

In one embodiment, a co-drug is represented by Formula (I) or Formula (II):

R—X—NH—CO—CO—OR¹ (I)

R—X—CO—O—CH₂—CO—OR¹ (II)

where

R is a tocol moiety, a tocol analog moiety, or a capsaicinoid moiety;

X is a direct bond or a linking group; and

OR¹ is the residue of an anticancer or antirestenotic agent bearing at least one hydroxyl group by which the CO—OR¹ ester linkage is formed.

In another embodiment, X is a linking group.

In another embodiment, X is a branched or unbranched hydrocarbyl moiety that may optionally include one or more in-chain or pendant heteroatom substituents and/or cyclic moieties.

In another embodiment, X is $[O(CH_2)_2]_n$, where n is an integer from 1 to 1000.

In another embodiment, n is 1.

In another embodiment, X is $O—CO(CH_2)_2[O(CH_2)_2]_n$, where n is an integer from 1 to 1000.

In another embodiment, X is $O—CO(CH_2)_m$ in which m is an integer from 1 to 12.

In another embodiment, m is 2.

In another embodiment, the co-drug is represented by Formula (I).

In another embodiment, the co-drug is represented by Formula (II).

In another embodiment, OR¹ is a residue of SN-22.

In another embodiment, R is a tocol analog moiety.

In another embodiment, R is a capsaicinoid moiety.

In another embodiment, the co-drug is represented by the formula R—O—CO(CH₂)₂—CO—O—CH₂—CO—OR¹ in which R is an α-tocopherol moiety and OR¹ is an SN-22 residue.

In another embodiment, the co-drug is represented by the formula R—O(CH₂)₂—NH—CO—CO—OR¹ in which R is an α-tocopherol moiety and OR¹ is an SN-22 residue.

In another embodiment, the co-drug is represented by the formula R—O(CH₂)₂—NH—CO—CO—OR¹ in which R is an α-tocopherol moiety and OR¹ is a podophyllotoxin residue.

In another embodiment, OR¹ is a podophyllotoxin residue.

Another embodiment is directed to a composition, comprising:

(a) a first co-drug as described above represented by Formula (I) or Formula (II), where —OR¹ of the first co-drug is a SN-22 residue; and (B) a second co-drug as described above represented by Formula (I) or Formula (II), where —OR¹ of the second co-drug is a podophyllotoxin residue.

In another embodiment, the first co-drug and the second co-drug of the composition described above are contained in nanoparticles.

Another embodiment is directed to nanoparticles comprising the co-drug as described above.

Another embodiment is directed to a method of treating a cancer patient, comprising administering to the cancer patient an effective amount of the co-drug as described above.

In another embodiment, the cancer patient is a human.

In another embodiment, the patient has neuroblastoma.

In another embodiment, the method of treating a cancer patient includes administering an effective amount of the composition described above to the patient.

In another embodiment, the method of treating a cancer patient includes an effective amount of the nanoparticles described above to the patient.

DETAILED DESCRIPTION

Figure 1:
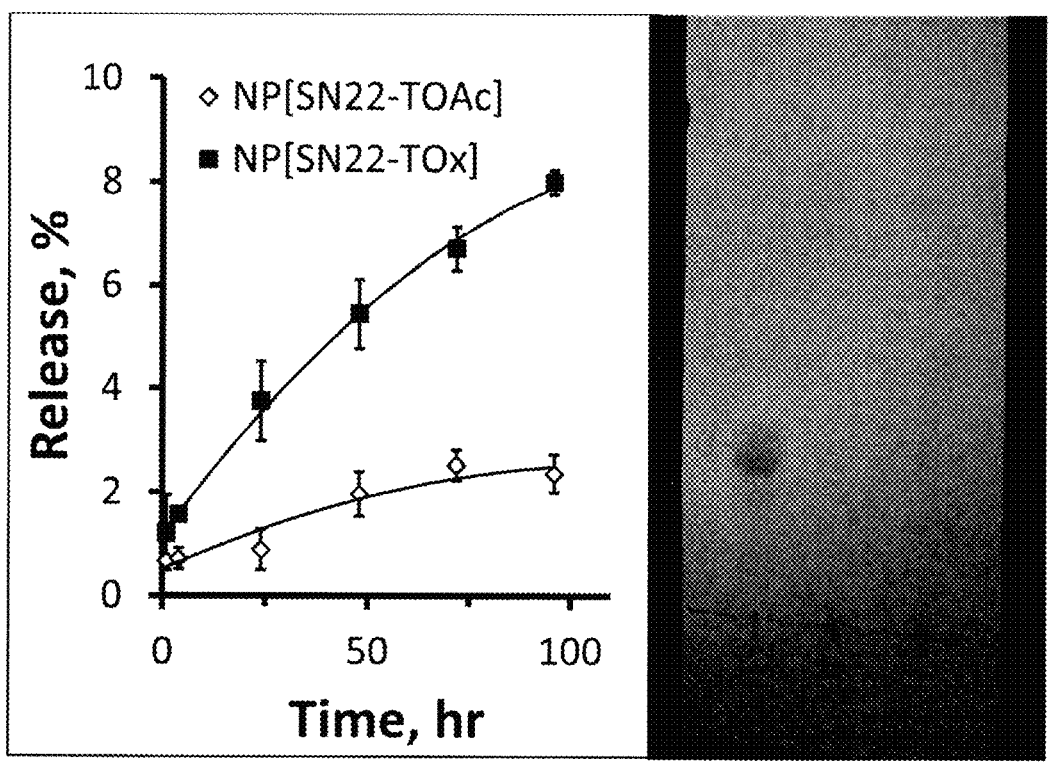
FIG. 1 shows release behavior of SN-22 co-drugs with different hydrolytic labilities measured under sink conditions.

The inventors have found that the co-drugs represented by Formula (I) and Formula (II) as described herein are especially suited for use as anticancer agents, and in particular, for the treatment of neuroblastoma.

In particular, the inventors have found that oxamate ester linkages are uniquely suited for creating rapidly activatable ester-linked co-drug conjugates between tocol, tocol analogs, or capsaicinoids and anticancer and/or antirestenotic agents having hydroxyl functions available for esterification. The accelerated hydrolytic activation of such conjugates is a special property of the oxamate esters not found in previously studied co-drug conjugates.

Co-drug conjugates according this description include oxamate esters represented by Formula (I),

R—X—NH—CO—CO—OR¹    (I)

wherein R is a tocol or tocol analog moiety or a capsaicinoid moiety, X is a direct bond or a linking group, and OR¹ is the residue of an anticancer or antirestenotic agent bearing at least one hydroxyl group by which the CO—OR¹ ester linkage is formed. All such co-drug conjugates can be prepared using methods analogous to those disclosed in the Examples and/or other methods known in the art, and all such conjugates and their therapeutic uses are contemplated herein.

Non-limiting examples of suitable anticancer or antirestenotic agents include paclitaxel, docetaxel, camptothecin, 7-ethyl-10-hydroxycamptothecin (SN-38), 7-ethylcamptothecin (SN-22), etoposide, fenretinide, and lestaurtinib. The hydroxyl group from which the OR¹ group is derived may be a phenolic or aliphatic hydroxyl group. Another suitable anticancer agent is podophyllotoxin (PPT), which may be used as the anticancer agent in Formula (I) or Formula (II).

The term "residue" of a compound as used herein, unless otherwise indicated, refers to an organic radical representing formal removal of an active hydrogen atom from a hydroxyl group on the compound. An example is the removal of a hydrogen atom from a carboxylic acid or an alcohol or phenol when forming an ester. The term applies regardless of whether the organic radical is actually obtained from the specified chemical species.

Tocol is 2-methyl-2-(4,8,12-trimethyltridecyl)-chroman-6-ol. Tocol analogs include all compounds containing a 2-methyl-2-(4,8,12-trimethyltridecyl)-chroman-6-ol moiety, including modifications thereof in which one or more methyl groups are on the benzene ring and/or in which the 4,8,12-trimethyltridecyl group is modified to include one or more in-chain olefinic double bonds. For example, there may be three methyl groups on the benzene ring and/or there may be three olefinic double bonds in the chain. Tocol analogs include any of a group of 8 naturally occurring fat soluble compounds with vitamin E activity. Examples include tocopherols and tocotrienols, with specific examples being α, β, γ and δ-tocopherol and α, β, γ and δ-tocotrienol.

The terms "tocol moiety," "tocol analog moiety," and "tocopherol moiety," etc., and minor variations thereof, refer herein to organic radicals representing formal removal of the 6-OH group from tocol, a tocol analog, and tocopherol, etc.

The term "capsaicinoid moiety" and minor variations thereof refers herein to organic radicals representing formal removal of the 4-OH group from a capsaicinoid, including from capsaicin itself. Nonlimiting examples of capsaicinoids other than capsaicin include dihydrocapsaicin, nordihydrocapsaicin, homodihydrocapsaicin, homocapsaicin, and nonivamide.

When X s a linking group, it may be a branched or unbranched hydrocarbyl moiety that may optionally include one or more in-chain or pendant heteroatom substituents and/or cyclic moieties. Typically, the hydrocarbyl moiety will comprise from 1 to 30 carbon atoms, or from 1 to 20, or from 1 to 10, or from 1 to 6. The number of carbon atoms may be 1, 2, 3, 4, or 5. Nonlimiting examples of X include [O(CH₂)₂]ₙ and O—CO(CH₂)₂[O(CH₂)₂]ₙ, where n in both cases is an integer with a lower limit of 1, 2, 3, or 4 and an upper limit of 1000, 500, 200, 100, 50, 25, or 10. The group X may be O—CO(CH₂)ₘ in which m is any integer from 1 to 12, or any sub-range thereof.

The inventors have now found that, in the context of co-drug construction for nanoparticle (NP)-based delivery, the strength of the co-drug-forming acid directly correlates with kinetics of the ester bond cleavage, thus providing an effective tool for controlling the co-drug fate and allowing its proper activation. Table 1 illustrates the effect of acid strength on rate of hydrolytic cleavage for several model compounds.

TABLE 1

| Type of ester bond | Model compound | $T_{1/2}$ for hydrolytic cleavage (pH 7) | Acid pKa |
| --- | --- | --- | --- |
| Acyl | CH₃COOEt | ~200 days | 4.7 |
| Oxyacetyl | CH₃OCH₂COOEt | 22 days | 3.6 |

TABLE 1-continued

| Type of ester bond | Model compound | $T_{1/2}$ for hydrolytic cleavage (pH 7) | Acid pKa |
|---|---|---|---|
| Acyloxyacetyl | $CH_3COOCH_2COOEt$ | 9 days | 2.7 |
| Oxamoyl | $CH_3NHCOCOEt$ | 17 hours | 1.8 |

Co-drug dissociation will result in formation of the two parent agents with respective log $P_{o/w}$ below the threshold required for stable entrapment in parenterally administered formulations (log $P_{o/w} \geq 9$). Released prematurely, they will lose the protection provided by the carrier against degradation and inactivation, and their pharmacokinetic disposition will reassume the uncontrolled (non-carrier) pattern. Therefore, the rate of co-drug cleavage needs to be tailored precisely to provide maximal drug regeneration within the target tissue while limiting off-target distribution and the loss of pharmacologic activity.

The redox-silent tocol/tocol analog/capsaicinoid compounds conjugated to anticancer or anitrestenotic agents via a hydrolytically cleavable bond form a co-drug that performs two complementary tasks. They (1) enhance nanoparticle-mediated delivery by modifying stability of the nanoparticle-cargo association and providing control over co-drug release and activation rates (i.e., a chemical moiety for reversible hydrophobization), and (2) function as a pharmacotherapeutic agent of the mitocan family (i.e., a mitochondrial-targeted drug) that works in concert with anticancer compound $R^1$.

In one example of a co-drug conjugate represented by Formula (I), referred to herein as SN22-TOx, R is an alpha-tocopherol moiety, X is $O(CH_2)_2$, and $OR^1$ is an SN-22 residue. Use of SN-22 can help address the problem of multi-drug resistance (MDR) seen with other camptothecin derivatives bearing phenolic hydroxyl groups, for example in patients with high-risk neuroblastoma (NB) in which the cancer cells express the "breast cancer resistance" protein ABCG2, which plays an important role in creating MDR. SN-22 is significantly less prone than phenolic camptothecin analogs to ABCG2-mediated resistance.

An additional significant advantage of SN-22 as the basis for co-drug design derives from its potentially more favorable biodisposition and extended retention in the target tissue. Lacking a phenolic hydroxyl group, it is not subject to enzymatic glucuronidation, which represents one of the main pathways for the rapid elimination of phenolic analogs (e.g., SN-38) from the body. Importantly, uridine diphosphate glucuronosyl transferase, the enzyme responsible for glucuronidation in normal tissues, is also present in a variety of solid tumors. This diminishes drug accumulation and retention in cancer cells and thereby contributes to chemotherapeutic drug resistance. Thus, the inventors believe that nanoparticles loaded with SN-22 based co-drugs will be especially effective at maintaining therapeutically adequate local drug levels for extended periods, which in turn should reduce systemic toxicity by allowing the use of smaller doses or less frequent dosing. The inventors also believe that co-drugs incorporating SN-22 moieties, in particular, can offer a significant therapeutic advantage by helping overcome multi-drug resistance (MDR).

Another embodiment provides a co-drug conjugate employing an acyloxyacetate linkage represented by Formula (II)

$$R—X—CO—O—CH_2—CO—OR^1 \quad (II)$$

wherein R, $R^1$, and X may be any combination of any of the variants described above with respect to the oxamate esters of Formula (I). The hydroxyl group from which the $OR^1$ group is derived may be a phenolic or aliphatic hydroxyl group. In particular, $OR^1$ may be an SN-22 residue and X may be $O—CO(CH_2)_m$ in which m is 2. In one example, the co-drug $R—O—CO(CH_2)_2—CO—O—CH_2—CO—OR^1$ in which R is an α-tocopherol moiety and $OR^1$ is an SN-22 residue.

In another embodiment —$OR^1$ represents a PPT residue. In particular, $OR^1$ may be a PPT residue and X may be $O—CO(CH_2)_m$ in which m is 2. In one example, the co-drug $R—O—CO(CH_2)_2—CO—O—CH_2—CO—OR^1$ in which R is an α-tocopherol moiety and $OR^1$ is an SN-22 residue.

In particular, a preferred embodiment is when the co-drug is represented by formula (I). In particular, in this embodiment X is a direct bond. Alternatively, X may be $O—CO(CH_2)_m$ in which m is 2. In any of these embodiments, $OR^1$ is an SN-22 residue or $OR^1$ is a PPT residue.

As discussed herein, the co-drugs may be incorporated into nanoparticles. The use of nanoparticles for drug delivery is well-known in the art. As such, the nature of the nanoparticles that may be used is not particularly limited. PEGylated biodegradable nanoparticles are preferred. The nanoparticles may also contain a carrier. For example, poly(D,L-lactide) or a poly(D,L-lactide)-poly(ethylene glycol) block copolymer are useful carriers. The nanoparticles may also be used in conjunction with one or more additives. Examples of suitable additives include trehalose and hydroxypropyl-β-cyclodextrin.

In one embodiment, a composition contains two or more co-drugs represented by Formula (I) and/or Formula (II). In a preferred example of this embodiment, at least two different co-drugs each represented by Formula (I) are used. In a preferred example of such an embodiment, the $OR^1$ of the first co-drug is a SN-22 residue and the second co-drug is a podophyllotoxin (PPT) residue. SN22-TOx and PPT-TOx as described herein are especially useful in such a composition. The weight ratio of the co-drugs may vary widely, such as 50:1, 20:1, 10:1, 5:1, 2:1, 1:1, 1:2, 5:1, 10:1, 20:1 and 50:1, including all specific values and subranges therebetween. The co-drugs may be incorporated into nanoparticles as discussed above.

The present disclosure is also directed to a method of treating cancer using the co-drugs and compositions as discussed above. The use of co-drug-charged nanoparticles as discussed above is an especially preferred embodiment. The patient may be a human but may also be an animal, such that the method can also be used in veterinary applications. The cancer may be neuroblastoma. The dosage of the co-drug(s) to be administered can be determined readily using techniques widely known in the art.

EXAMPLES

The co-drug $R—O—CO(CH_2)_2—CO—O—CH_2—CO—OR^1$ in which R is an α-tocopherol moiety and $OR^1$ is an SN-22 residue can be prepared by the following method. First, 3-(D-α-Tocopheryloxycarbonyl)propionyloxyacetic acid is prepared from the commercially available D-α-tocopheryl hemisuccinic acid. Briefly, tetrabutylammonium D-α-tocopheryl hemisuccinate is reacted with tert-butyl bromoacetate in 1-methyl-2-pyrrolidone (1-MP), with subsequent removal of the tert-butyl group with trifluoroacetic acid/triethylsilane in dichloromethane to yield the acid. SN-22 is then conjugated to this acid according to a standard procedure using 1-ethyl-3-(3-dimethylaminopropyl)carbodiimide hydrochloride (EDC) as a promoter and 4-N,N-dimethylamino-pyridine tosylate (DPTS) as a catalyst in dichloromethane as a solvent.

SN22-TOx was obtained using a similar process. PPT-TOx can also be prepared in this manner. First, N-(2-D-α-Tocopheryloxy)ethyloxamic acid was prepared in an overall yield of 79% from D-α-tocopherol first treated with tetrabutylammonium hydroxide and reacted with bromoacetonitrile in 1-MP. The resulting D-α-tocopheryloxyacetonitrile was then reduced to 2-(D-α-tocopheryloxy)ethylamine with lithium aluminium hydride in ethyl ether. The amine was acylated with methyl chlorooxoacetate, forming methyl N-(2-D-α-tocopheryloxy)ethyloxamate, which was hydrolyzed with water/potassium carbonate to form N-(2-D-α-tocopheryloxy)ethyloxamic acid.

Then, SN-22 was conjugated with the N-(2-D-α-tocopheryloxy)ethyloxamic acid according to the standard procedure with EDC as a promoter and DPTS as a catalyst in dichloromethane as a solvent, and its structure and purity was confirmed by $^1$H NMR and TLC (yield: 63%).

The SN-22 ester of tocopheryl oxyacetic acid (SN22-TOAc) was obtained by acylating SN-22 with D-α-tocopheryloxyacetic acid in 95% yield according to a standard procedure, using 1-ethyl-3-(3-dimethylaminopropyl)-carbodiimide hydrochloride (EDC) as a promoter and 4-N,N-dimethylamino-pyridine tosylate (DPTS) as a catalyst. The structure and purity were confirmed by $^1$H NMR and TLC.

Nanoparticles (NP) containing SN22-TOAc and SN22-TOx were each formulated with a 90-95% yield (corresponding to a loading of 16-17% w/w or 4.0-4.2 mg per ml) and characterized as previously described. See Alferiev I S, Iyer R, Croucher J L, Adamo R F, Zhang K, Mangino J L, Kolla V, Fishbein I, Brodeur G M, Levy R J, Chorny M. Nanoparticle-mediated delivery of a rapidly activatable prodrug of SN-38 for neuroblastoma therapy. Biomaterials 2015; 51:22-29, and Iyer R, Croucher J L, Chorny M, Mangino J L, Alferiev I S, Levy R J, Kolla V, Brodeur G M.

PEGylated biodegradable nanoparticles were prepared using a modified nanoprecipitation method optimized for producing ultrasmall particulates. A 20 mg portion of SN22 conjugate with tocopherol oxyacetate or oxamate (SN22-TOAc or SN22-TOx, respectively), 100 mg of poly(D,L-lactide)-b-poly(ethylene glycol) (5 kDa:5 kDa) and 20 mg of PLURONIC® F-68 surfactant were dissolved in 8 mL of acetone, and 12 mL of ethanol was added to the organic phase. The organic phase was rapidly added to 50 mL water with magnetic stirring. The mixture was transferred into an evaporation flask, and the solvents were removed by gradually reducing the pressure from 130 mbar to 40 mbar at 30° C. The formulation was additionally concentrated, trehalose and hydroxypropyl-β-cyclodextrin (5% and 7% w/v, respectively) were added to the nanoparticle suspension, and the volume was adjusted to 5.0 mL. The resulting nanoparticles were sterilized by passing them through a 0.22 µm filter unit, and then freeze-dried in sterile containers.

Blank NP were used as a negative control, and unmodified SN-22, diluted in cell culture medium from a DMSO stock, was used as a positive control.

Release studies using an external sink method showed highly distinct behaviors, with a markedly faster rate observed for the more labile SN22-TOx (p<0.0001, regression analysis).

FIG. 1 shows release behavior of SN-22 co-drugs with different hydrolytic abilities measured under sink conditions (37° C., acceptor medium: heptane/methyl tert-butyl ether, 1:1 v/v; left panel). Release samples were also analyzed by TLC (right panel). The results suggest that co-drug cleavage contributes to the faster release observed with NP[SN22-TOx] (lane 3 vs. 2). Free SN-22 is included in lane 1.

The results of release studies (FIG. 1) are consistent with the concept that faster release from nanoparticles should result from using more hydrolytically labile co-drug constructs, due to accelerated co-drug cleavage to form the parent compound, which lacks the hydrophobicity required for stable retention in nanoparticles. Indeed, the faster release exhibited by NP[SN22-TOx] vs. NP[SN22-TOAc] was paralleled by notably larger amounts of SN-22 observed in the respective acceptor medium samples (FIG. 1, right panel; compare lanes 3 and 2).

Figure 2:
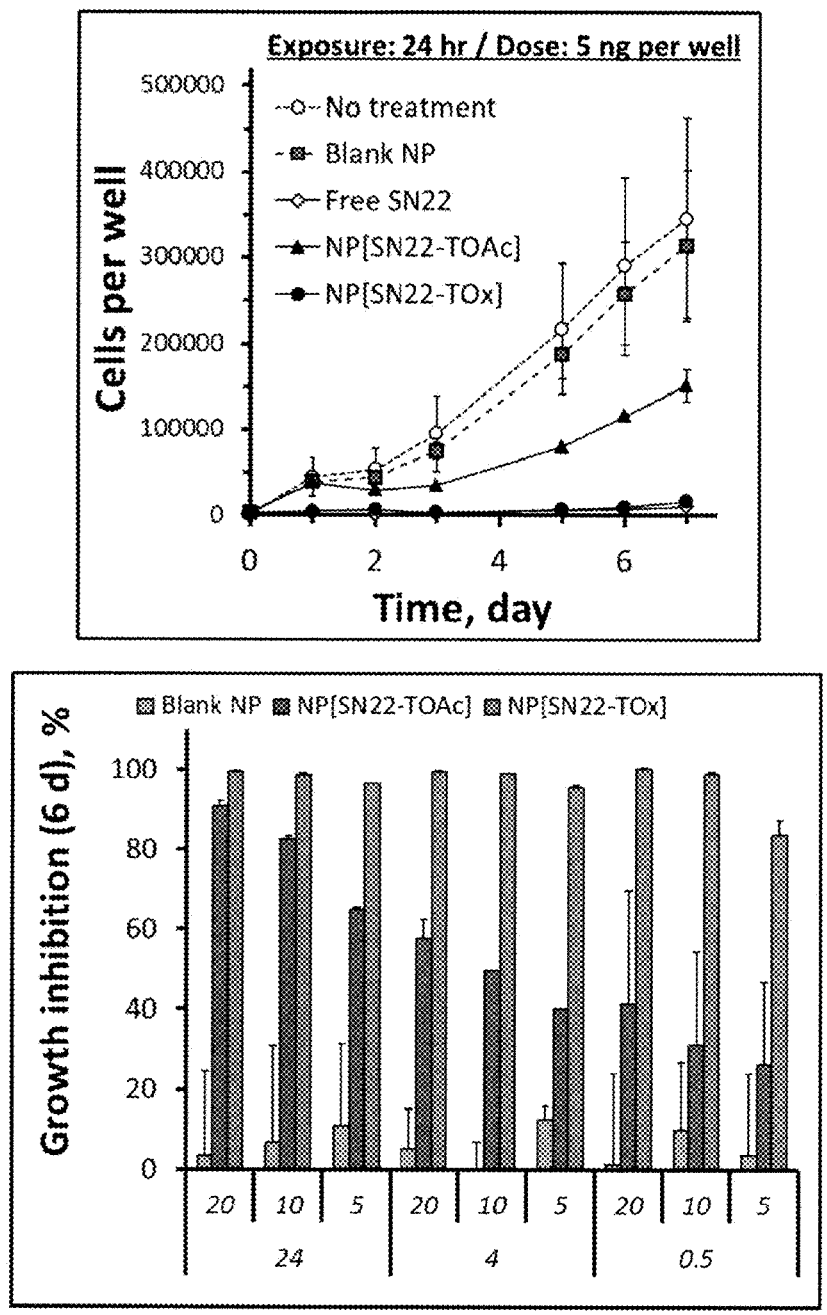
FIG. 2 shows comparative antiproliferative effects of nanoparticles loaded with SN22-TOAc vs. SN22-TOx on MYCN-amplified neuroblastoma cells.

FIG. 2 shows comparative antiproliferative effects of nanoparticles loaded with SN22-TOAc vs. SN22-TOx on MYCN-amplified NB cells (IMR-32, ATCC CCL-127™). Cell growth curves of NB cells treated with co-drug loaded nanoparticles at doses corresponding to 5 ng SN-22 per well (96-well plates) for 24 hours are shown in comparison to "no treatment", drug-free nanoparticles and free SN-22 (upper panel). Cell growth inhibition (%) determined 6 days post-treatment is shown for co-drug loaded and drug-free (control) nanoparticles as a function of dose and exposure duration (lower panel).

In agreement with observed differences in release and drug activation kinetics, NP[SN22-TOx] applied to MYCN-amplified NB cells (IMR-32, ATCC CCL-127™) inhibited proliferation almost completely, whereas only partial (dose- and exposure duration-dependent) growth inhibition was observed with NP[SN22-TOAc] (FIG. 2). Equivalent doses of free SN-22 (5-20 ng per well) or drug-free (blank) nanoparticles resulted in a fully inhibited cell growth and a marginal antiproliferative effect, respectively (FIG. 2). Together with the results of release studies, these findings confirm the more stable retention of the less hydrolytically labile SN22-TOAc in nanoparticles, compared with the much faster release of SN-22 from NP[SN22-TOx] due to rapid hydrolysis of the SN22-TOx.

Figure 3:
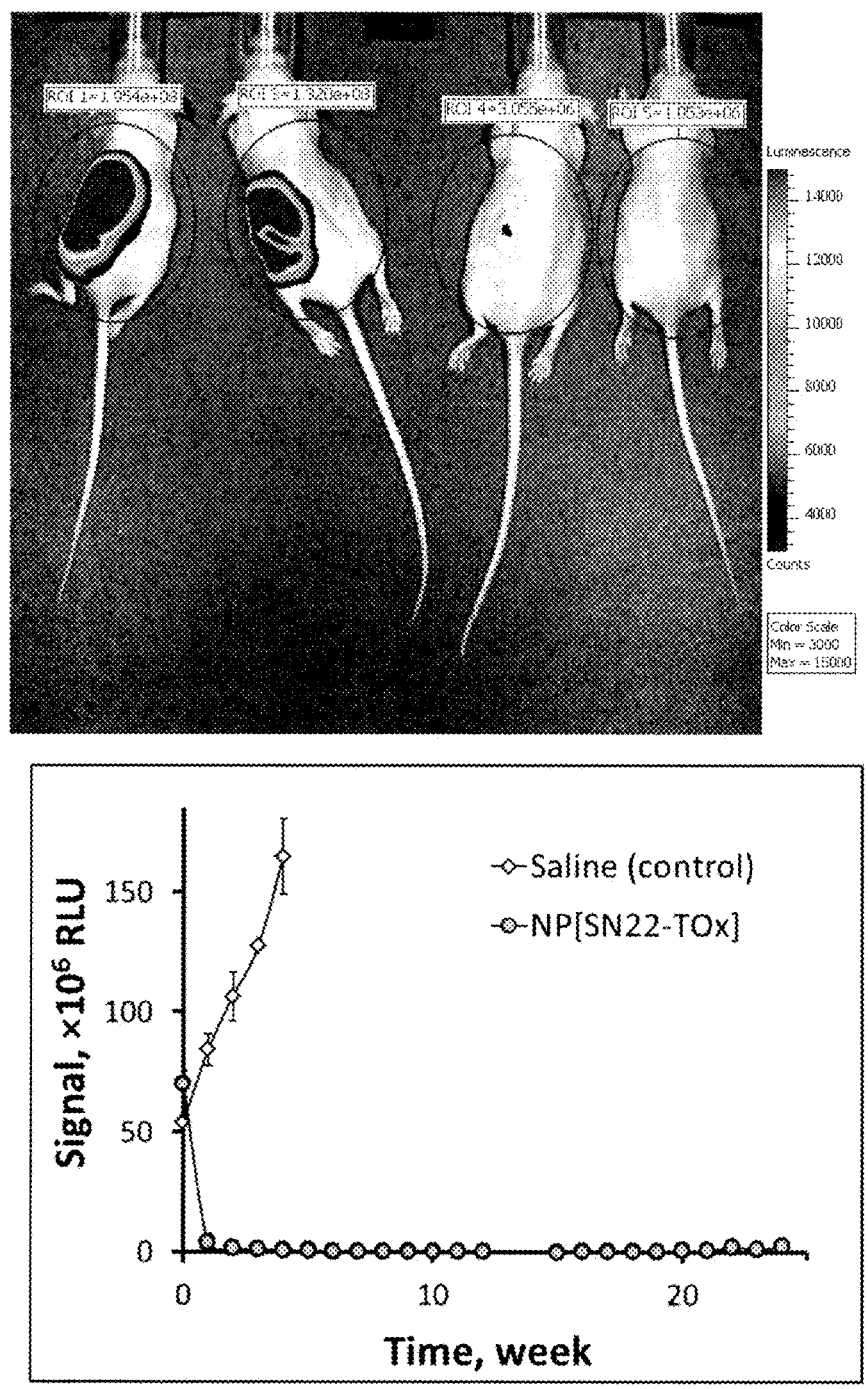
FIG. 3 shows the therapeutic efficacy of nanoparticles loaded with SN22-TOx in an orthotopic mouse model of high-risk neuroblastoma.

FIG. 3 shows the therapeutic efficacy of NP[SN22-TOx) in an orthotopic mouse model of high-risk NB. Mice were inoculated with IMR-32 cells stably expressing luciferase. Treatment with NP[SN22-TOx] (vs. saline as a control) was initiated at a dose equivalent to 200 µg SN-22 per injection IV, once a week for 4 weeks. Tumor-associated signal was monitored by weekly by bioluminescence. Images taken 28 days after treatment initiation are in the upper panel. Data are shown in the lower panel, presented as mean±SD. The tumor-associated signal rapidly declined in animals receiving weekly IV injections of NP[SN22-TOx] (dose equivalent to 200 µg SN-22 per injection) and remained uniformly low during the course of treatment and over an additional 21 weeks after the treatment was discontinued (FIG. 3). This is in contrast to a steady increase in signal and growth of readily palpable tumors observed in control animals administered with saline.

These results confirm that nanoparticles loaded with a reversibly hydrophobized co-drug of SN-22 can deliver, release and maintain therapeutically adequate amounts of the active parent compounds within the tumor, causing regression and inhibiting regrowth of MYCN-amplified orthotopic xenografts, demonstrating feasibility of the SN-22 co-drug/nanoparticle combination approach as a treatment for high-risk NB. Further, any of the co-drugs described herein may be used to treat NB or cancers in general, with or without incorporating the co-drugs in nanoparticles. If the co-drug is incorporated in nanoparticles, the nanoparticles may also comprise a carrier, for example poly(D,L-lactide) or a poly(D,L-lactide)-poly(ethylene glycol) block copolymer. The present disclosure therefore provides a method of treating a cancer patient by administering an effective amount of a co-drug, or administering nanoparticles comprising such co-drugs.

What is claimed:

1. A co-drug according to Formula (I) or Formula (II),

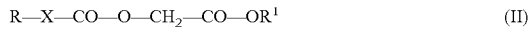

wherein:
R is a tocol moiety, a tocol analog moiety, or a capsaicinoid moiety;
X is a direct bond or $[O(CH_2)_2]_n$, where n is an integer from 1 to 1000; and
$OR^1$ is the residue of an anticancer or antirestenotic agent bearing at least one hydroxyl group by which the $CO-OR^1$ ester linkage is formed.

2. The co-drug according to claim 1 wherein X is $[O(CH_2)_2]_n$.

3. The co-drug according to claim 1 wherein n is 1.

4. The co-drug according to claim 1 wherein the co-drug is according to Formula (I).

5. The co-drug according to claim 1 wherein the co-drug is according to Formula (II).

6. The co-drug according to claim 1 wherein $OR^1$ is a residue of SN-22.

7. The co-drug according to claim 1 wherein R is a tocol analog moiety.

8. The co-drug according to claim 1 wherein R is a capsaicinoid moiety.

9. A co-drug $R-O-CO(CH_2)_2-CO-O-CH_2-CO-OR^1$ in which R is an α-tocopherol moiety and $OR^1$ is an SN-22 residue.

10. A co-drug $R-O(CH_2)_2-NH-CO-CO-OR^1$ in which R is an α-tocopherol moiety and $OR^1$ is an SN-22 residue.

11. Nanoparticles comprising a co-drug according to claim 1.

12. A method of treating a cancer patient, comprising administering an effective amount of a co-drug according to claim 1.

* * * * *